United States Patent
Kuehn

(10) Patent No.: US 8,521,286 B2
(45) Date of Patent: *Aug. 27, 2013

(54) LEAD-CARRIED PROXIMAL ELECTRODE FOR QUADRIPOLAR TRANSTHORACIC IMPEDANCE MONITORING

(75) Inventor: Kevin P. Kuehn, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 28 days.

This patent is subject to a terminal disclaimer.

(21) Appl. No.: 13/099,940

(22) Filed: May 3, 2011

(65) Prior Publication Data

US 2011/0208262 A1    Aug. 25, 2011

Related U.S. Application Data

(63) Continuation of application No. 11/343,897, filed on Jan. 31, 2006, now Pat. No. 7,937,150.

(51) Int. Cl.
*A61N 1/372* (2006.01)

(52) U.S. Cl.
USPC .............................. 607/28; 607/36

(58) Field of Classification Search
USPC ................ 607/18, 28, 36, 115, 116, 119
See application file for complete search history.

(56) References Cited

U.S. PATENT DOCUMENTS

| | | |
|---|---|---|
| 5,284,136 A | 2/1994 | Hauck et al. |
| 5,331,966 A | 7/1994 | Bennett et al. |
| 5,476,496 A | 12/1995 | Strandberg et al. |
| 5,562,711 A | 10/1996 | Yerich et al. |
| 5,707,398 A | 1/1998 | Lu |
| 6,161,042 A | 12/2000 | Hartley et al. |
| 6,278,894 B1 | 8/2001 | Salo et al. |
| 6,334,071 B1 | 12/2001 | Lu |
| 6,512,949 B1 | 1/2003 | Combs et al. |
| 6,795,733 B1 | 9/2004 | Lu |
| 6,912,420 B2 | 6/2005 | Scheiner et al. |
| 7,191,009 B2 | 3/2007 | Laske et al. |
| 2001/0002000 A1 | 5/2001 | Kumar et al. |
| 2002/0042634 A1 | 4/2002 | Bardy et al. |
| 2002/0147475 A1 | 10/2002 | Scheiner et al. |
| 2004/0098054 A1 | 5/2004 | Eckerdal et al. |
| 2004/0215240 A1* | 10/2004 | Lovett et al. ............... 607/4 |
| 2005/0283197 A1 | 12/2005 | Daum et al. |
| 2005/0288600 A1 | 12/2005 | Zhang et al. |

FOREIGN PATENT DOCUMENTS

WO    WO 9833553    8/1998

OTHER PUBLICATIONS

Daum et al., "Hemodynamic Sensors," Nov. 2, 2000, Am J Cardiol 2000, vol. 86, (Suppl), pp. 95k-100k.
International Search Report, PCT/US2007/060582, Jun. 19, 2007, 7 pages.

* cited by examiner

*Primary Examiner* — Allen Porter, Jr.
(74) *Attorney, Agent, or Firm* — Carol F. Barry

(57) ABSTRACT

An implantable medical device (IMD) provides quadripolar transthoracic impedance measurement capability by forming at least one of the two electrodes associated with the canister of the device on a lead proximate the canister.

15 Claims, 3 Drawing Sheets

LEAD-CARRIED PROXIMAL ELECTRODE FOR QUADRIPOLAR TRANSTHORACIC IMPEDANCE MONITORING

RELATED APPLICATION

This application is a continuation of U.S. patent application Ser. No. 11/343,897, filed Jan. 31, 2006 entitled "LEAD-CARRIED PROXIMAL ELECTRODE FOR QUADRIPOLAR TRANSTHORACIC IMPEDANCE MONITORING", which has been allowed as U.S. Pat. No. 7,937,150, and issuing on May 3, 2011, herein incorporated by reference in its entirety.

BACKGROUND OF THE INVENTION

The present invention relates to an electrode configuration for a system that performs quadripolar transthoracic impedance monitoring.

Many implantable medical devices (IMDs) such as pacemakers, defibrillators, and others, are configured to measure transthoracic impedance via a function known as impedance minute ventilation (IMV) sensing. In some devices, the measured transthoracic impedance is used to adjust the rate of cardiac pacing, and many other uses of the measured transthoracic impedance are being implemented or contemplated, including pulmonary edema monitoring, sleep apnea monitoring and detection, respiration monitoring, measurement of mechanical cardiac functions, and others.

Transthoracic impedance measuring is performed by monitoring the voltage differential between pairs of spaced electrodes as current pulses are injected into leads connected to the electrodes. For example, a current pulse may be delivered between a ring electrode of a pacemaker and the conductive canister of the pacemaker, and a voltage differential may be measured between a tip electrode of the pacemaker and the conductive canister. This arrangement is referred to as a tripolar measurement system. It has been found that another desirable configuration of electrodes is one in which two independent sets of electrodes are used, known as a quadripolar measurement system. In a quadripolar system, two electrically isolated electrodes are provided at the canister of the device, which can add complexity to the design of the device.

BRIEF SUMMARY OF THE INVENTION

The present invention is an implantable medical device (IMD) that provides quadripolar transthoracic impedance measuring capability by forming an electrode on a lead proximate to the device canister. In this way, the cost and complexity of providing two electrodes local to the canister are reduced in comparison to a configuration having two electrically isolated electrodes provided on the device canister.

DETAILED DESCRIPTION

Figure 1:
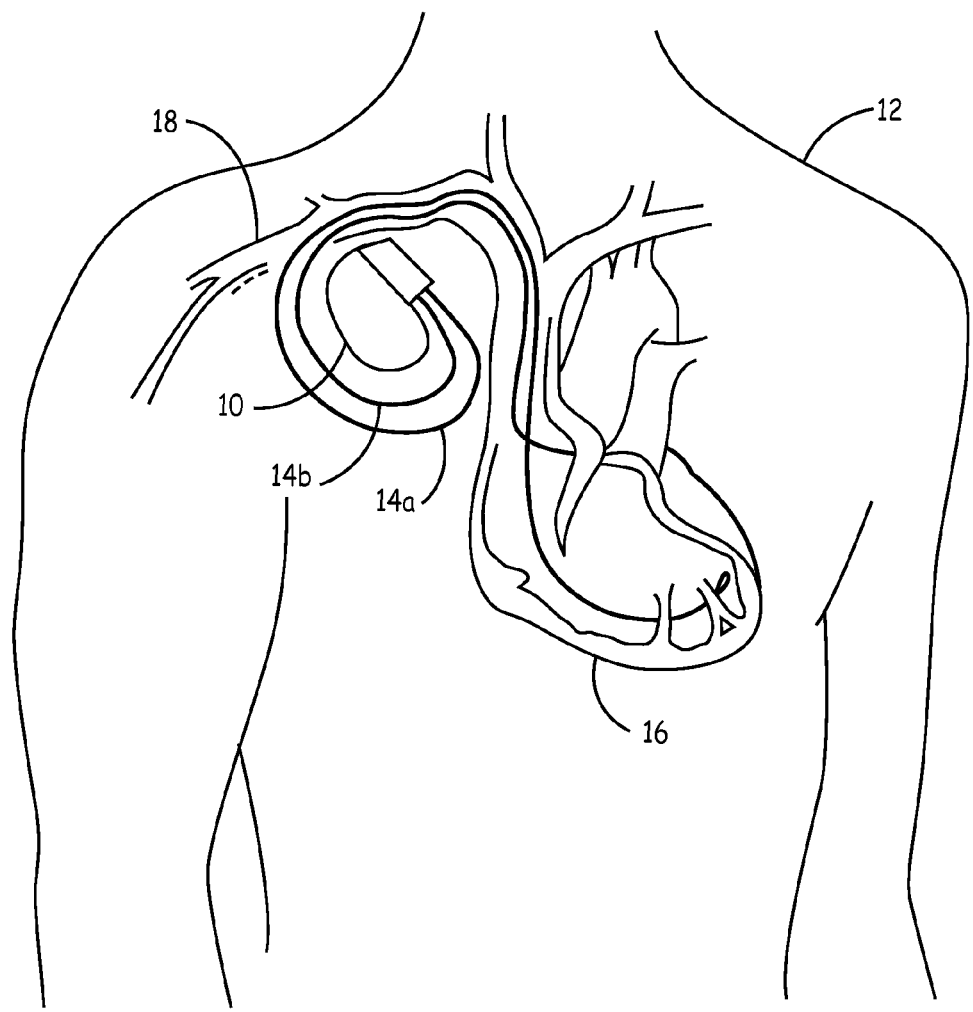
FIG. 1 is an illustration of an implantable medical device (IMD) such as a pacemaker that has been implanted into a human body.

FIG. 1 is an illustration of implantable medical device (IMD) 10 that has been implanted into human body 12. As is known in the art, IMD 10 is housed within a hermetically sealed, biologically inert outer canister. In some embodiments, the outer canister of IMD 10 is composed of a conductive material, and may serve as an indifferent electrode in the sensing circuitry of IMD 10. Leads 14a and 14b are electrically coupled to IMD 10 in a conventional manner, extending to another part of body 12, such as into heart 16 via vein 18. IMD 10 is illustrated in FIG. 1 as being an implantable pacemaker (with lead 14a having ventricular sense/pace electrodes at its distal end and lead 14b having atrial sense/pace electrodes at its distal end), although it should be understood that the principles of the present invention (described below) are applicable to other implantable medical devices as well. For example, the distal ends of leads 14a and 14b may be implanted subcutaneously in any number of locations, rather than located in the ventricle and atrium of a patient's heart.

Figure 2:
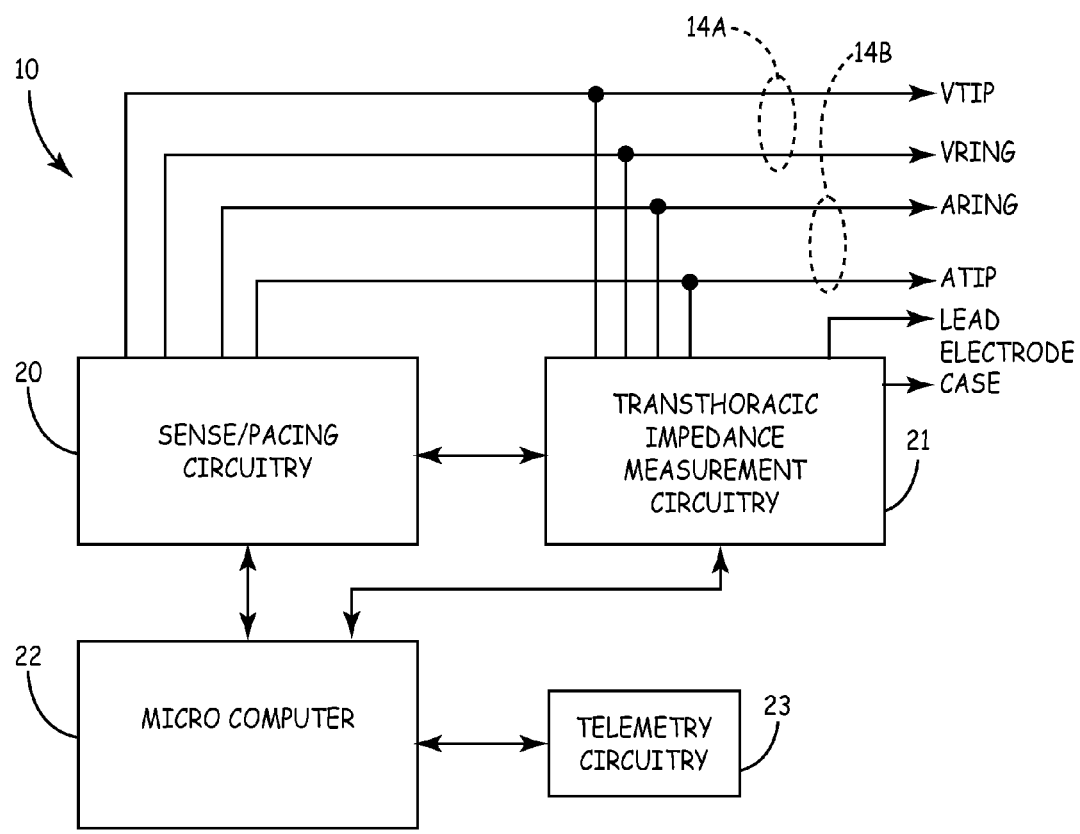
FIG. 2 is a block diagram illustrating the functional components of an IMD such as a pacemaker that is capable of measuring transthoracic impedance.

FIG. 2 is a block diagram illustrating the functional components of IMD 10 (shown as a pacemaker), including the components that provide the capability of measuring transthoracic impedance. IMD 10 includes sense/pacing circuitry 20, transthoracic impedance measurement circuitry 21, microcomputer 22, and telemetry circuitry 23. Microcomputer 22 is coupled to communicate with sense/pacing circuitry 20, transthoracic impedance measurement circuitry 21 and telemetry circuitry 23, and sense/pacing circuitry 20 and transthoracic impedance measurement circuitry 21 are coupled to one another and to leads 14A and 14B. The internal details of sense/pacing circuitry 20, transthoracic measurement circuitry 21, microcomputer 22 and telemetry circuitry 23 are conventional in design, and are omitted from this discussion for purposes of clarity.

In operation, sense/pacing circuitry 20 senses cardiac electrical signals from, and delivers pacing pulses to, ventricular electrodes VTIP and VRING and atrial electrodes ATIP and ARING. Microcomputer 22 operates to process and store sensed cardiac electrical signals, and controls the functions of sense/pacing circuitry. Transthoracic impedance measurement circuitry 21 injects current pulses into lead 14A and/or 14B, and measures the voltage difference between a distal electrode (i.e., VTIP, VRING, ATIP or ARING) and a local electrode (i.e., LEAD ELECTRODE or CASE). Because two independent electrodes associated with the canister of IMD 10 are provided, it is possible to inject current pulses between one local electrode (e.g., CASE) and one distal electrode (e.g., VRING), and to measure the voltage differential between a different local electrode (e.g., VTIP) and a different local electrode (e.g., LEAD ELECTRODE). This quadripolar measurement configuration has been found to be advantageous. Microcomputer 22 operates to process and store the sensed transthoracic impedance, and in some embodiments has the ability to adjust the operation of sense/pacing circuitry 20 based on the measured transthoracic impedance. Information can also be received by microcomputer or transmitted by microcomputer to external devices via telemetry circuitry 23.

As discussed above, transthoracic impedance measurement circuitry 21 is shown with a quadripolar configuration, employing two independent electrodes (labeled LEAD ELECTRODE and CASE) in the local vicinity of the case (canister) of IMD 10. In existing systems, the canister of IMD 10 is specially designed to provide these two independent electrodes, electrically insulated from one another. For example, one or both of the electrodes may be provided as "dot" electrodes on the surface of the canister of IMD 10, with insulating material surrounding the electrode(s), or one or both of the electrodes may be provided inside the canister of IMD 10 in an insulating mounting arrangement. Designs such as these require customization in the design of IMD 10, which can add expense and complexity to the manufacturing process.

According to an embodiment of the present invention, at least one of the local electrodes proximate the canister of IMD 10 is provided on one or more of leads 14A and 14B. This configuration reduces the expense and complexity involved in customizing the design of IMD 10, since it is less expensive and complex to provide a customized lead that allows quadripolar transthoracic impedance monitoring to be performed.

Figure 3:
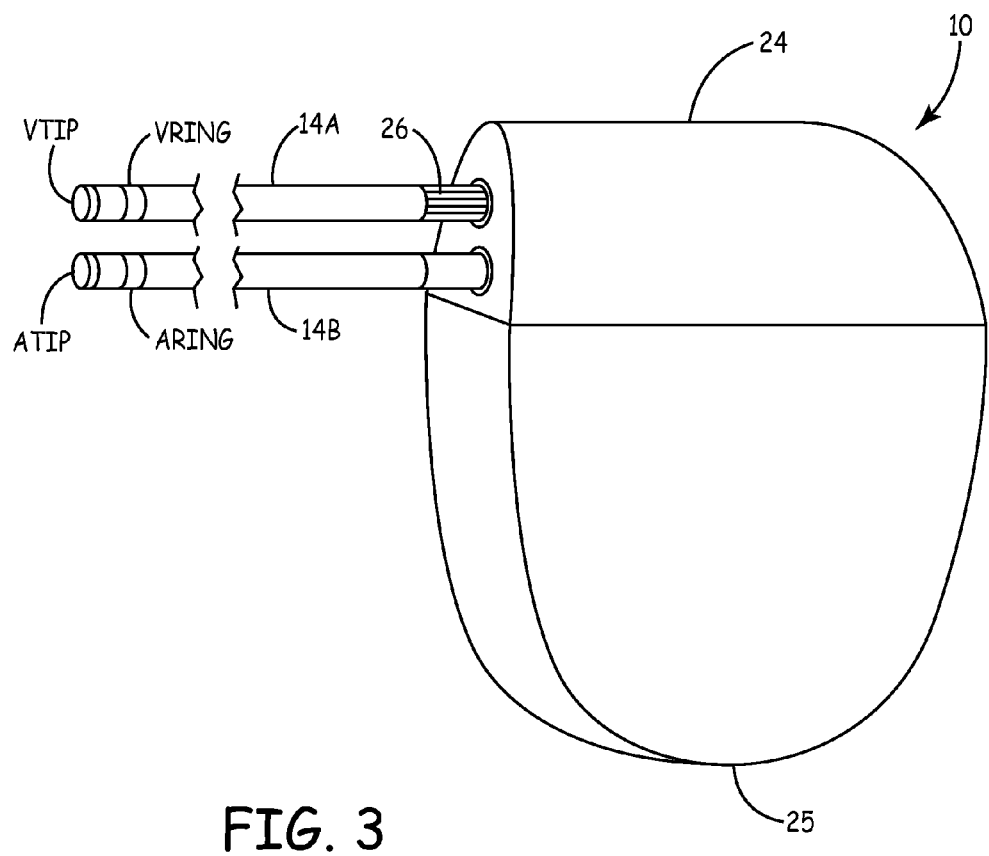
FIG. 3 is a diagram illustrating a quadripolar electrode configuration of an IMD according to an embodiment of the present invention.

FIG. 3 is a diagram illustrating a quadripolar electrode configuration of IMD 10 according to an embodiment of the present invention. IMD 10 includes a package having header 24 and canister 25. Ventricular lead 14A and atrial lead 14B are received by header 24 in a manner generally known in the art, to connect to the internal circuitry (such as sense/pacing circuitry 20 and transthoracic impedance measurement circuitry 21 shown in FIG. 2) of IMD 10.

As shown in FIG. 3, lead 14A includes electrode 26 formed on the lead in close proximity to header 24. This placement of electrode 26 provides one of the two local electrodes (i.e., electrode LEAD ELECTRODE shown in FIG. 2) for quadripolar transthoracic impedance measurement. The other local electrode (i.e., electrode CASE shown in FIG. 2) is provided by canister 25 of IMD 10, for example. Placing electrode 26 in close proximity to the receiving bore of header 24 maintains the two local electrodes in close proximity to one another, which is desirable for quadripolar transthoracic impedance measurement, and prevents electrode 26 from shorting to header 24 due to flexing of lead 14A. In an alternative embodiment, both local electrodes could be provided on leads adjacent to header 24.

By providing at least one of the local electrodes (i.e., electrode 26) on lead 14A rather than in the design of the canister of IMD 10, the cost and complexity of employing a quadripolar transthoracic impedance monitoring configuration can be decreased. Implementing a customized lead (i.e., lead 14A with electrode 26 formed on it) is relatively simple and inexpensive compared to customizing the design of the canister of IMD 10, and still provides all of the desirable performance of quadripolar transthoracic impedance monitoring.

Although the present invention has been described with reference to preferred embodiments, workers skilled in the art will recognize that changes may be made in form and detail without departing from the spirit and scope of the invention. For example, one skilled in the art will recognize that other types of implantable medical devices and lead implantation locations, in addition to the examples described herein, can be employed in various embodiments while practicing the principles of the invention.

What is claimed is:

1. In an implantable medical device (IMD) which comprises a canister, a header coupled to the canister, first and second local electrodes, at least one lead having a proximal end received by the header and a distal end, the at least one lead having first and second distal electrodes, and transthoracic impedance measurement circuitry coupled to the first and second local electrodes and the first and second distal electrodes to perform quadripolar measurements of transthoracic impedance, the improvement comprising:
providing at least one of the first and second local electrodes on the at least one lead adjacent to the header such that the local electrode is prevented from shorting to a portion of the canister due to flexing of the at least one lead carrying the local electrode.

2. The IMD of claim 1, wherein the first local electrode is provided on the at least one lead adjacent to the header such that the first local electrode is prevented from shorting to a portion of the canister due to flexing of the at least one lead carrying the first local electrode and the second local electrode is provided by the header.

3. An implantable medical device (IMD) having quadripolar transthoracic impedance measurement capability, comprising:
a canister;
a header coupled to the canister;
a first lead having a proximal end received by the header and a distal end, the first lead carrying a first distal ring electrode, a first distal tip electrode, and a proximal electrode positioned adjacent the header such that the proximal electrode is prevented from shorting to a portion of the canister due to flexing of the first lead carrying the proximal electrode;
a second lead received by the header, the second lead carrying a second distal ring electrode and a second distal tip electrode; and
transthoracic impedance measurement circuitry coupled to the canister and the electrodes carried by the first and second leads, wherein the transthoracic impedance measurement circuitry is configured to perform quadripolar measurements of transthoracic impedance using the canister, the proximal electrode, and any two of the first distal ring electrode, the first distal tip electrode, the second distal ring electrode and the second distal tip electrode.

4. The IMD of claim 3, wherein the first lead is implantable in a ventricle and the second lead is implantable in an atrium.

5. The IMD of claim 3, wherein the first lead is implantable in an atrium and the second lead is implantable in a ventricle.

6. The IMD of claim 3, wherein the proximal electrode is located on the first lead adjacent to a bore in the header that receives the first lead.

7. The IMD of claim 3, further comprising:
sense/pacing circuitry coupled to the first and second leads and to the transthoracic impedance measurement circuitry.

8. The IMD of claim 7, further comprising:
a microcomputer coupled to the sense/pacing circuitry and to the transthoracic impedance measurement circuitry.

9. The IMD of claim 8, wherein the sense/pacing circuitry is adjustable in response to measurements performed by the transthoracic impedance measurement circuitry.

10. The IMD of claim 7, further comprising:
telemetry circuitry coupled to the microcomputer.

11. The IMD of claim 3, wherein the proximal electrode rests immediately adjacent to the header.

12. The IMD of claim 3, wherein the canister provides a first local electrode configured to be used to provide quadripolar transthoracic impedance measurements, wherein the proximal electrode carried on the first lead positioned adjacent to the header provides a second local electrode configured to be used to provide quadripolar transthoracic impedance measurements, and further wherein the transthoracic impedance measurement circuitry is configured to perform quadripolar measurements of transthoracic impedance using at least the first local electrode provided by the canister, the second local electrode provided by the proximal electrode carried at a position adjacent the header, and one or more of the distal electrodes.

13. In an implantable medical device (IMD) which comprises a canister, a header coupled to the canister, first and second local electrodes, at least one lead having a proximal end and a distal end, the proximal end coupled to the header, the at least one lead having first and second distal electrodes, and transthoracic impedance measurement circuitry coupled to the first and second local electrodes and the first and second distal electrodes to perform quadripolar measurements of transthoracic impedance, the improvement comprising:

providing at least one of the first and second local electrodes on the at least one lead adjacent to the header such that the local electrode is prevented from shorting to a portion of the canister due to flexing of the at least one lead carrying the local electrode.

14. An implantable medical device comprising:
a housing;
a processor disposed in the housing;
a transthoracic impedance circuit coupled with the processor for selectively delivering current pulses;
a header coupled to the housing;
an atrial lead having a proximal end coupled to the header and a distal end, the atrial lead operatively coupled with the processor and the transthoracic impedance circuit, the atrial lead includes one or more electrodes;
a ventricular lead having a proximal end coupled to the header and a distal end, the ventricular lead operatively coupled with the processor and the transthoracic impedance circuit, the ventricular lead includes one or more electrodes,
wherein the housing and one of the electrodes on either the atrial lead or the ventricular lead positioned adjacent the header such that the electrode is prevented from shorting to a portion of the canister due to flexing of the lead carrying the electrode are used as local electrodes along with any two other electrodes on the atrial lead or ventricular lead in determining quadripolar measurements of transthoracic impedance.

15. The device of claim 14, wherein the electrode on either the atrial lead or the ventricular lead positioned adjacent the header such that the electrode is prevented from shorting to a portion of the canister due to flexing of the lead carrying the electrode is proximate to a bore on the header.

* * * * *